(12) United States Patent
Rosenberg

(10) Patent No.: US 7,575,094 B1
(45) Date of Patent: *Aug. 18, 2009

(54) STETHOSCOPE COVER INCORPORATED INTO AN ISOLATION GARMENT

(76) Inventor: Tova Rosenberg, 11930 Kling St., Apt. 17, Valley Village, CA (US) 91607

( * ) Notice: Subject to any disclaimer, the term of this patent is extended or adjusted under 35 U.S.C. 154(b) by 0 days.

This patent is subject to a terminal disclaimer.

(21) Appl. No.: 11/901,107

(22) Filed: Sep. 13, 2007

Related U.S. Application Data

(63) Continuation-in-part of application No. 11/127,371, filed on May 11, 2005, now Pat. No. 7,296,652.

(51) Int. Cl.
*A61B 7/02* (2006.01)

(52) U.S. Cl. .................. 181/131; 2/250; 2/10; 2/94
(58) Field of Classification Search .................. 181/131
See application file for complete search history.

(56) References Cited

U.S. PATENT DOCUMENTS

| | | | |
|---|---|---|---|
| 4,791,681 A * | 12/1988 | Dean | 2/106 |
| 5,072,456 A | 12/1991 | Elin | |
| 5,142,702 A * | 9/1992 | Piloian | 2/102 |
| 5,466,898 A | 11/1995 | Gilbert | |
| 5,548,842 A * | 8/1996 | Wiseman, Sr. | 2/69 |
| D376,043 S * | 12/1996 | Rix | D3/203.1 |
| 5,623,131 A * | 4/1997 | Earnest | 181/131 |
| 6,006,856 A * | 12/1999 | Skubal et al. | 181/131 |
| 6,154,888 A * | 12/2000 | Krohn | 2/250 |
| 6,687,919 B2 * | 2/2004 | Dilworth et al. | 2/457 |
| 6,763,527 B1 * | 7/2004 | Rivoli et al. | 2/250 |
| 7,296,652 B1 * | 11/2007 | Rosenberg | 181/131 |
| 2002/0170771 A1 * | 11/2002 | Milam et al. | 181/131 |

* cited by examiner

*Primary Examiner*—Jeffrey Donels
*Assistant Examiner*—Forrest M Phillips
(74) *Attorney, Agent, or Firm*—Thomas I. Rozsa

(57) ABSTRACT

A stethoscope cover incorporated into an isolation garment which cover operably retains the stethoscope listening device and at least a portion of the stethoscope sound tube so that a doctor or nurse can put on an isolation garment and use their preferred stethoscope to examine a patient because the portions of the stethoscope which come in contact with a patient or are near the patient are protected from coming directly in contact with the patient by the stethoscope cover. Preferred embodiments include having the opening of the stethoscope cover attached at the neck opening of the isolation garment or attached at a location below the neck opening.

6 Claims, 5 Drawing Sheets

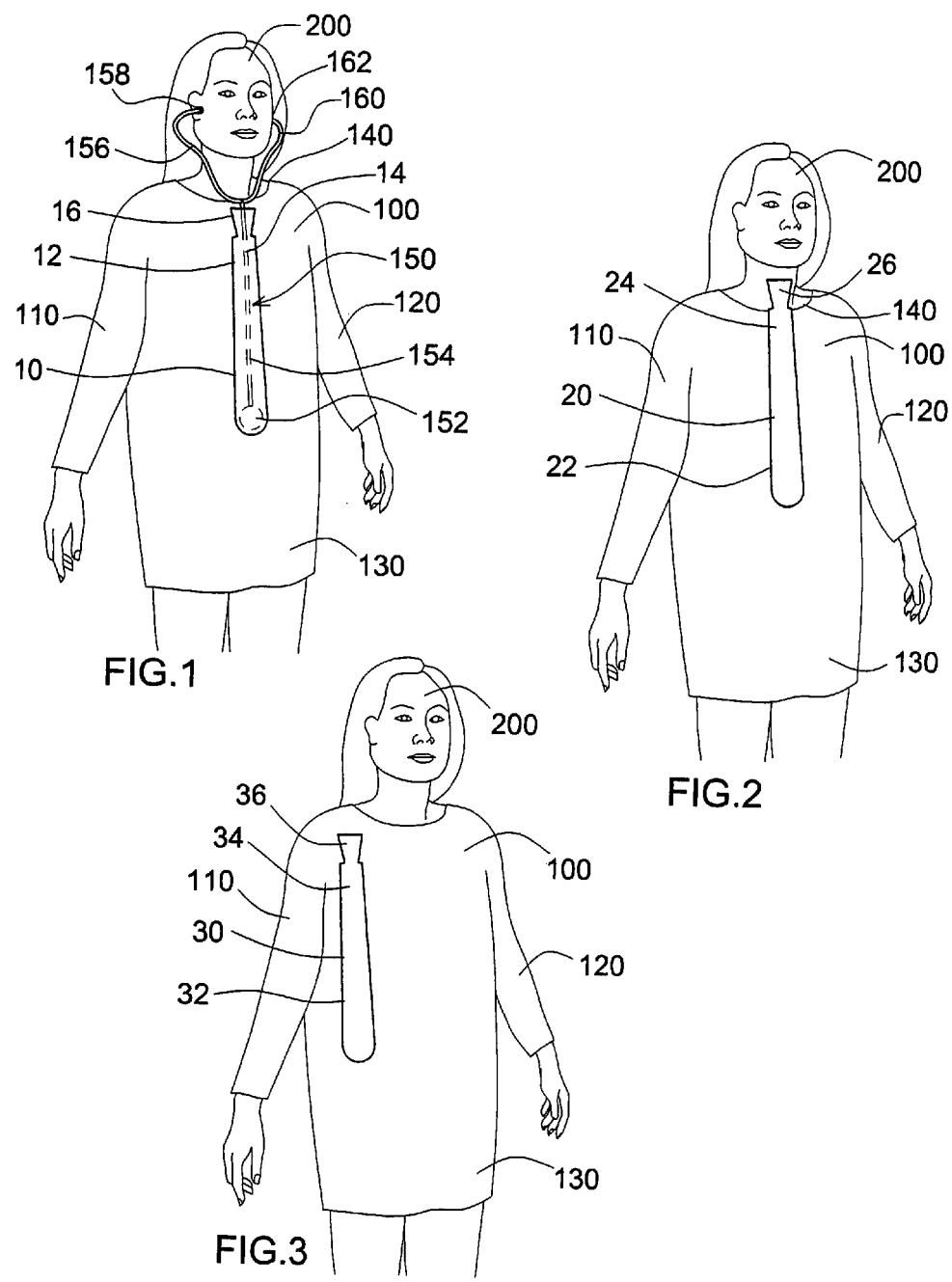

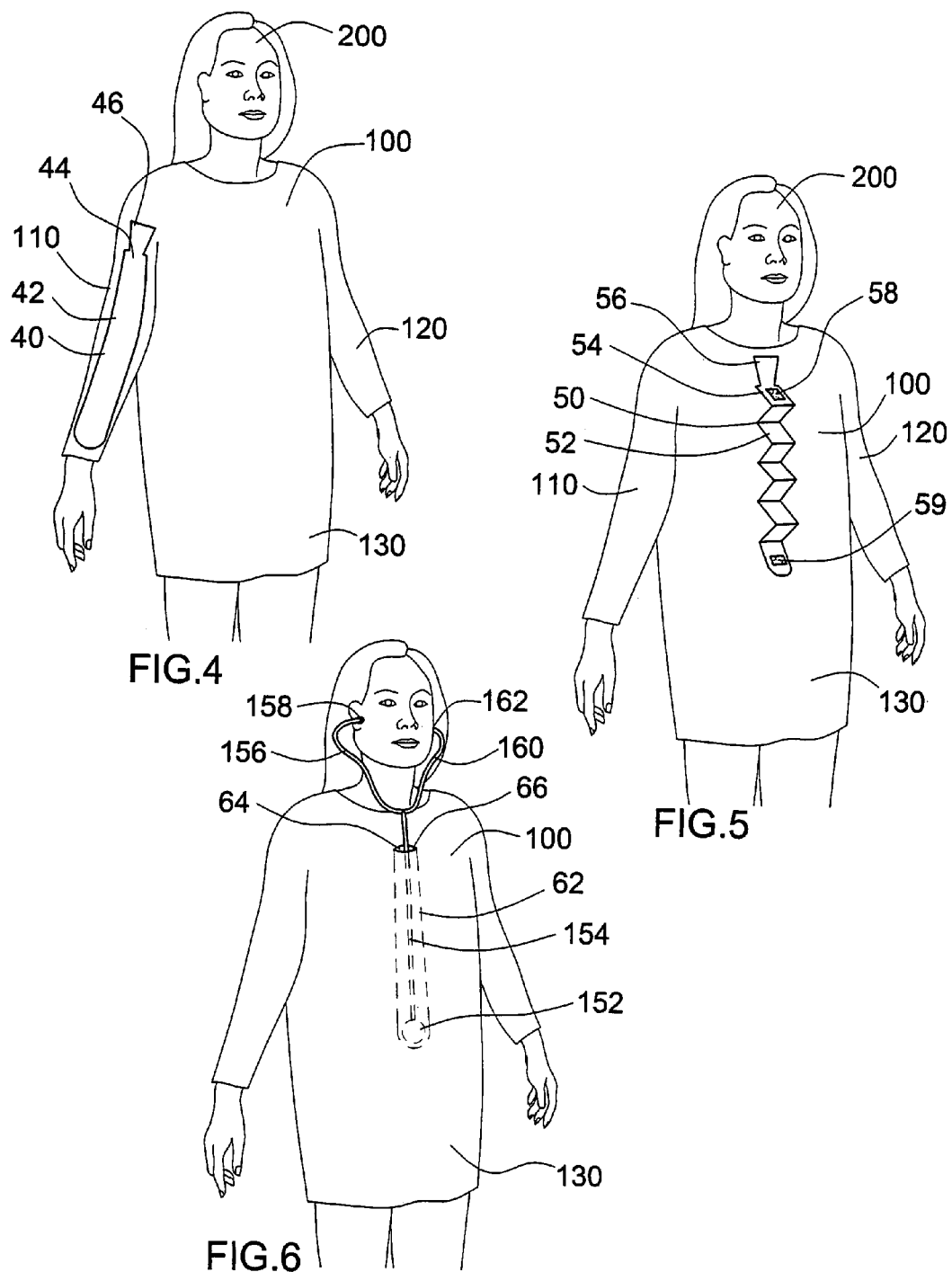

STETHOSCOPE COVER INCORPORATED INTO AN ISOLATION GARMENT

This patent application is a continuation-in-part of patent application Ser. No. 11/127,371 filed May 11, 2005 now U.S. Pat. No. 7,296,652.

BACKGROUND OF THE INVENTION

1. Field of the Invention

The present invention relates to medical device coverings to prevent transmission of biological infection and contamination and more particularly pertains to a protective stethoscope cover for enclosing portions of a stethoscope which ordinarily come in contact with a patient who may have a communicable disease.

2. Description of the Prior Art

In general, the broad concept of having a cover for a stethoscope is known in the prior art. The following nine patents and published patent applications are relevant to the field of the present invention.

1. U.S. Pat. No. 5,072,456 issued to Elin on Dec. 17, 1991 for "Outerwear Garment For Ems Personnel" (hereafter the "Elin Patent");

2. U.S. Pat. No. 5,466,898 issued to Gilbert on Nov. 14, 1995 for "Stethoscope Isolation System" (hereafter the "Gilbert Patent");

3. U.S. Pat. No. 5,548,842 issued to Wiseman on Aug. 27, 1996 for "Protective Garment With Harness Access" (hereafter the "Wiseman Patent");

4. U.S. Pat. No. Des. 376,043 issued to Rix on Dec. 3, 1996 for "Stethoscope Cover" (hereafter the "Rix Patent");

5. U.S. Pat. No. 5,623,131 issued to Earnest on Apr. 22, 1997 for "Protective Stethoscope Cover Having A Head Cover Connected To A Body Cover" (hereafter the "Earnest Patent");

6. U.S. Pat. No. 6,006,856 issued to Skubal on Dec. 28, 1999 for "Stethoscope Sheathing System" (hereafter the "Skubal Patent");

7. U.S. Pat. No. 6,154,888 issued to Krohn on Dec. 5, 2000 for "Stethoscope Pocket" (hereafter the "Krohn Patent");

8. U.S. Patent Application Publication No. US 2002/0170771 A1 to Milam on Nov. 21, 2002 for "Protective Cover For Stethoscope, And Dispensing Assembly Comprising Same" (hereafter the "Milam Patent Publication");

9. U.S. Pat. No. 6,763,527 B1 issued to Rivoli on Jul. 20, 2004 for "Medical Assistant Outer Garment" (hereafter the "Rivoli Patent").

The Elin Patent discloses an outerwear garment which includes a tool holster panel that includes a plurality of pockets each adapted to receive a piece of emergency medical equipment. The garment is intended to be worn by emergency medical personnel and has a multiplicity of pockets in order to enable them to quickly reach into and obtain medical equipment for use in an emergency. With respect to the discussion of a stethoscope, as depicted in FIG. 1, hip length coat 10 includes a zippered upper right front stethoscope pocket 61. However, while the stethoscope can be retained in the pocket, it cannot be used while in the pocket and must be removed from the pocket and used in a conventional way.

The Gilbert Patent essentially discloses a stethoscope isolation system which includes a stethoscope sheath so that the stethoscope can be used while it is in the sleeve. Referring to FIGS. 1a through 1c, the invention includes a sleeve 1 wherein there is a first (2) and second (3) ends. The sleeve 1 has formed therein a cavity 4 for accepting the lower end of a stethoscope, the cavity being surrounded by a wall 5 of fluid, bacterial, and virally impermeable fabric, paper, or the like, composed of first (1) and second (11) sides. The invention discloses the concept of having a sleeve which covers the stethoscope so that the stethoscope will not come in contact with the patient but the doctor holds the stethoscope sleeve in his hand while examining the patient.

The Wiseman Patent discloses the concept of an attachment to a garment but the attachment has a harness access. Flexible harness conduit assembly 20 is attached to torso section 14 of the protective garment. Flexible harness conduit assembly 20 includes flexible harness conduit 21 attached at one end to a hole (not shown) through torso section 14 by means of attachment patch 22. In this case, the attachment is for a safety harness and it is not used with a stethoscope.

The Rix Patent is a design patent which is a stethoscope cover wherein the stethoscope is placed within the protective cover and the ear pieces protrude out through the cover so that they can be connected to the doctor's ears. Once again, this is a separate cover by itself and is not attached to a garment.

The Earnest Patent is also a protective cover for a stethoscope. The cover encloses a center sound tube and head of a stethoscope. The head cover can be extended over the head of a stethoscope and may be separated from or coupled to the center sound tube cover. A cover flap can extend over an upper end of the center sound tube cover and between lateral sound tubes of the stethoscope to include an unintentional engagement with hair. As best illustrated in FIGS. 1 and 2, it can be shown that the sound tube cover 12 of the present invention 10 preferably comprises an elongated flexible sheath 18 having a transverse dimension sufficient to receive a head 20 of the stethoscope 16 therethrough during installation of the device 10 relative to a stethoscope. As shown in FIGS. 5 and 6, an alternative embodiment of the invention 10 may comprise coupling of the elastic neck opening 32 of the semi-spherical cover 30 to the elastic collar 22 of the flexible sheath 18. By this structure, both the head 20 and the center sound tube 14 can be fully enclosed within the present invention 10. However, once again, what is not shown is that the sheath is sewn onto a garment but it is simply a separate sheath which is separately handled by the doctor.

The Skubal Patent is also a stethoscope sheathing system which includes an elastic sheath and a retaining ring which is provided for a stethoscope having a head, a sound tube and an ear piece. The sheath has an open end for admittance of the head and a portion of the sound tube and a closed end. The sheath is sized such that the head of the stethoscope and at least a portion of the sound tube is enveloped by the sheath. Once again, this is a sheath for use with a stethoscope but the sheath itself is not connected to a garment.

The Krohn Patent does disclose the concept of having a protective sheath sewn onto a garment, in this case a pant leg, but the purpose is to simply house the stethoscope and it cannot be used in its operating condition when in the sheath. In the Krohn invention, a pocket is added to a scrub pant that is suitable for carrying an unfolded stethoscope. The outline of the pocket approximates, and is larger than, the shape of the unfolded stethoscope. The pocket totally encloses the stethoscope. The pocket provides a convenient safe and sanitary place for the stethoscope. However, the stethoscope cannot be used in its operating condition when in the pocket, and the stethoscope must be removed from the pocket when used.

The Milam Published Patent Application discloses a protective cover for a stethoscope which has an elongated bag and a closed first end and is either fully or partially opened at the second opposite end to form an enclosed container for retaining the head and sound piece of the stethoscope. The invention relates to a protective cover which is useful for preventing the stethoscope contamination and transmission of infectious organisms and other biohazards as well as to an assembly for dispensing the same. The protective cover article may be formed of any material, preferably comprising material that is acoustically transmitting and impermeable to bacteria, viruses and fluids. Once again, this is a protective cover for a stethoscope but it is not attached to a garment.

The Rivoli Patent is a medical assistant torso outer garment configured with multiple organizational pockets for securing and carrying medical instruments including a stethoscope. Looking at FIG. 8, the spacing of each double pocket 40 from the neck opening 22 and the vertical centerline 42 is selected such that opposite ends of a stethoscope 32 centrally placed around a wearer's neck would naturally come to rest in, and occupy a substantial portion of each double pocket 40. In this case, the garment enables a way to carry the stethoscope but once again, the stethoscope cannot be used when it is in the pockets and the pockets are simply meant to carry the stethoscope and cannot be used in the operating condition.

There is a significant need for an improved stethoscope cover which can be incorporated into a garment that enables the stethoscope to be used in its operative condition.

SUMMARY OF THE INVENTION

The present invention is a stethoscope cover incorporated into an isolation garment which cover operably retains the stethoscope listening device and at least a portion of the stethoscope sound tube so that a doctor or nurse can put on an isolation garment and use their preferred stethoscope to examine a patient because the portions of the stethoscope which come in contact with a patient or are near the patient are protected from coming directly in contact with the patient by the stethoscope cover.

It has been discovered, according to the present invention, that if a stethoscope cover is incorporated into and made a part of an isolation garment, then it can very efficiently be used to retain a stethoscope that the doctor or nurse prefers to use because it is not necessary to search for or locate a separate stethoscope cover which is an item separate and apart from the isolation garment.

It has further been discover, according to the present invention, that by having a stethoscope cover which is incorporated into and made a part of the isolation garment, the doctor or nurse does not have to use disposable stethoscopes, but can use their own preferred stethoscope with at least a portion of the stethoscope including the listening device and a portion of the center sound tube retained in the interior chamber of the stethoscope cover so that after the examination of the patient with an infectious disease has concluded, the stethoscope can be removed and the entire isolation garment including the incorporated stethoscope cover can be disposed of.

It has further been discovered, according to the present invention, that by having a stethoscope cover incorporated into an isolation garment, the doctor or nurse will be more inclined to want to use their own preferred stethoscope and it will not be necessary for them to hunt for a separate stethoscope cover as the entire cover of the stethoscope is incorporated into and made a part of the isolation garment.

It has additionally been discovered, according to the present invention, that the stethoscope cover can be incorporated into the isolation garment by being a part of or attached to a portion of the torso section either in the middle of the isolation garment or on either side of the isolation garment or adjacent the neck opening of the isolation garment and can further be attached to either sleeve of the isolation garment and can be used in an operative condition in this manner.

It has additionally been discovered, according to the present invention, that the stethoscope cover can be incorporated into the torso section of the isolation garment such that the opening lies adjacent the neck opening of the isolation garment so that the stethoscope immediately goes into the stethoscope cover from adjacent the wearer's neck area. Also, the opening can be positioned slightly lower than the neck area so that the stethoscope can go into the stethoscope cover at a location slightly below the neck area.

It has further been discovered, according to the present invention, that the stethoscope cover can also be incorporated into an opening in the isolation garment and retained in an interior sheath within the isolation garments.

It is therefore an object of the present invention to provide a fully incorporated stethoscope cover incorporated into and made a part of an isolation garment so that a doctor or nurse can use their preferred stethoscope by having the listening device and a portion of the center sound tube retained in the stethoscope cover which is a part of the isolation garment so that the portions of the stethoscope which come in contact with or adjacent a patient who may have an infectious disease are concealed and protected by the stethoscope cover.

It is a further object of the present invention to provide an efficient system for being able to reuse the same stethoscope in a situation with infectious disease patients by having a stethoscope cover incorporated into and made a part of and/or attached to and be a part of, the isolation garment so that the stethoscope portions which come in contact with or are adjacent to the patient are concealed and protected by the stethoscope cover and the stethoscope cover enables the stethoscope to be used in a fully operative condition because the lateral sound tubes and air piece which do not come adjacent the patient can be used by the doctor in the ordinary way while the flexible stethoscope cover which is attached to the isolation garment permits the stethoscope operating portions which are the listening device and center sound tube to be used in the ordinary way and still be fully protected from coming in contact with the patient.

It is an additional object of the present invention to include a stethoscope cover which can be incorporated into any usable location of an isolation garment or attached to any usable location of an isolation garment including any portion on the torso, whether it be the center portion, the left or right portion, or adjacent the neck opening portion, or any portion of either sleeve of the isolation garment.

It is an additional object of the present invention to provide a stethoscope cover which can be incorporated into the torso section of the isolation garment such that the opening lies adjacent the neck opening. of the isolation garment so that the stethoscope immediately goes into the stethoscope cover from adjacent the wearer's neck area. Also, the opening can be positioned slightly lower than the neck area so that the stethoscope can go into the stethoscope cover at a location slightly below the neck area.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIG. 1 is a perspective view of one embodiment of the present invention stethoscope cover incorporated into an isolation garment with the portion of the stethoscope which is enclosed in the cover shown in dashed lines, the cover being attached to the center area of the torso;

FIG. 2 is a perspective view of a second embodiment of the present invention stethoscope cover incorporated into an isolation garment with the cover attached adjacent the neck opening in the isolation garment, the cover being attached to the center area of the torso;

FIG. 3 is a perspective view of a third embodiment of the present invention stethoscope cover incorporated into an isolation garment with the cover attached to a portion of one side of the torso;

FIG. 4 is a is a perspective view of a fourth embodiment of the present invention stethoscope cover incorporated into an isolation garment with the cover attached to a portion of the sleeve;

FIG. 5 is a is a perspective view of a fifth embodiment of the present invention stethoscope cover with the cover being in an accordion shaped fold up condition when not in use with the cover unfolded for receiving a stethoscope for the in use condition;

FIG. 6 is a is a perspective view of a sixth embodiment of the present invention stethoscope cover with the cover being incorporated into an interior sleeve in the isolation garment;

DETAILED DESCRIPTION OF THE PREFERRED EMBODIMENTS

Figure 7:
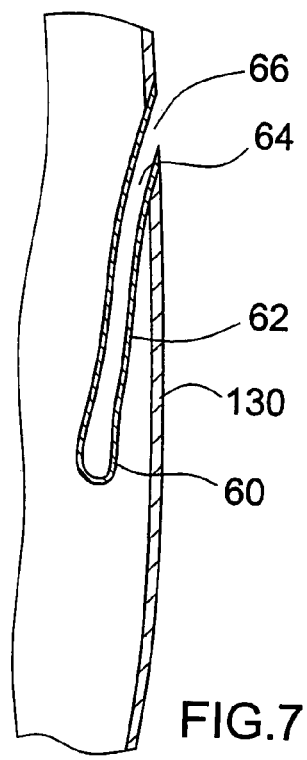
FIG. 7 is a cross-sectional view of the sixth embodiment of the present invention stethoscope cover illustrated in FIG. 6.

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is a solution to the following problem. In a hospital when going into an isolation room where a patient may have either a communicable disease or some other ailment wherein there is no desire to have the ailment or any portion of the disease transferred out of the room, the people walking into the room wear what is called an isolation garment which is generally yellow but can also be any other color such as white or other color and is made of a special material which covers all parts of their bodies. In addition to that, they will wear gloves and a mask.

However, the key concept here involves the use of stethoscopes. One solution to the problem is to have what is called disposable stethoscopes wherein the stethoscope is made of disposable material and is used to listen to the patient's heart and other organs during a customary medical examination and thereafter discarded. However, most doctors don't like to use the disposable stethoscope and instead, prefer to use their regular stethoscope. The problem with that is that with a regular stethoscope, it cannot be reused over and over again because it comes in contact with the patient. Therefore, the present invention addresses the concept of incorporating into the isolation garment a pouch to house the stethoscope so that the end tip and front portion of the stethoscope which either come in contact with the patient or come near the patient will be housed within the pouch, whereas the portions that go into the doctor's ears can be close to the doctor's ears with a covering disposable cap. However, the innovation of the present invention is to have sewn or otherwise attached onto the garment at any location, but preferably on the front, a pouch which houses the stethoscope in a usable operative condition and is sufficiently long so that the doctor can use the stethoscope in the pouch to come in contact with the patient to listen to the patient's vital organs.

Variations to the concept of the pouch include the following. The pouch can be accordion shape, the pouch can be generally elongated or the pouch can be any other type of shape. While preferably on the center of the garment, it can be housed on either sleeve or at any other location on the garment. Once the examination is finished, the entire garment including the pouch is discarded and the stethoscope can be reused over and over again since it did not come in direct contact with the patient having the disease.

Referring to FIG. 1, when going into an isolation room to examine a patient who has a communicable disease, a doctor 200 wears what is known as an isolation garment 100. In addition to wearing the isolation garment 100, the doctor 200 also has a mask (not shown) covering the doctor's face and disposable gloves (not shown) protecting and covering the doctor's. hands. As a general rule, the isolation garment 100 is yellow in color and is made of any type of protective material which is relatively inexpensive and is disposable. The isolation garment has a first sleeve 110 and a second sleeve 120 and a front torso portion 130 with a neck opening 140. The isolation garment 100 can be of one piece construction so that the doctor 200 fits his/her hands and arms through the sleeves 110 and 120 and puts his/her head through the neck opening 140 and fits the isolation garment 100 over his/her torso. Alternatively, the isolation garment 100 may be open at the back and tied at the back with a disposable tie member which comes affixed to the isolation garment 100. For purposes of the present invention, the key components of the isolation garment 100 and the torso portion 130, the neck opening 140, and the sleeves 110 and 120. Also, while the isolation garment 200 is illustrated as being worn by a doctor, it is understood that this isolation garment is also worn by nurses and any other person who goes into the room where there is a patient with a communicable disease.

A stethoscope 150 has a head or listening device 152 connected to a center sound tube 154 which in turn is connected to a first lateral sound tube 156 which terminates in a first ear piece 158 and a second lateral sound tube 160 which terminates in a second ear piece 162.

The concept of the present invention is to have a sheath or pouch incorporated into the isolation garment and preferably made of the same material as the material of the isolation garment with the sheath being affixed to the isolation garment in a manner to permit at least the listening device 152 and center sound tube 154 to be received in and retained by the sheath so that the stethoscope is in the usable and operative condition and can be used by the doctor or nurse to listen to body parts of the patient while the doctor or nurse 200 is wearing the isolation garment 100. In the figures, there are illustrated alternative variations of different embodiments of this concept and different ways of attaching the sheath to the isolation garment. It will be appreciated that these are illustrations of the concept of the present invention and other variations of design or attachment location or method of attachment of the sheath incorporated into an isolation garment for housing a stethoscope in the usable and operative condition are within the spirit and scope of the present invention.

A first embodiment of a stethoscope cover or sheath 10 is illustrated in FIG. 1. The sheath 10 has an elongated sheath section 12 having an elongated interior chamber 14 which is open at the top. Optionally, the elongated sheath section 12 can have incorporated into its exterior a front covering flap 16. In the first embodiment, the sheath 12 is attached adjacent its upper interior portion to the central upper area of torso portion 130 and the isolation garment in the area of the doctor's breastplate.

Figure 8:
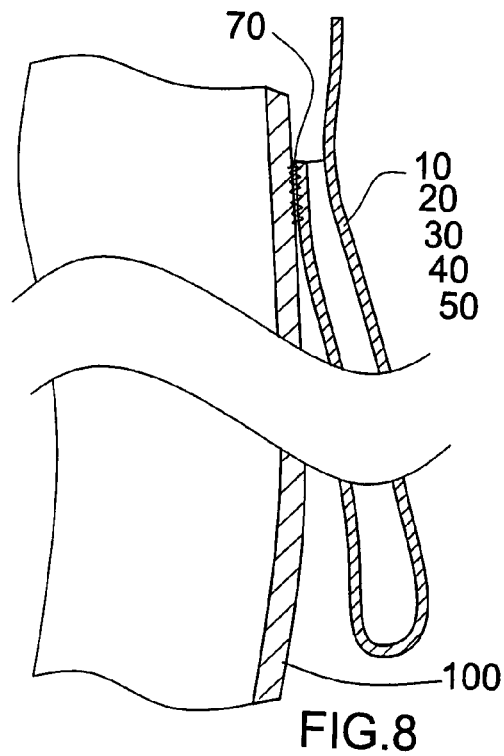
FIG. 8 is a cross-sectional view of one attachment method for attaching any of the embodiments illustrated in FIGS. 1 through 5 which illustrates heat sealing the stethoscope cover to the isolation garment.
Figure 9:
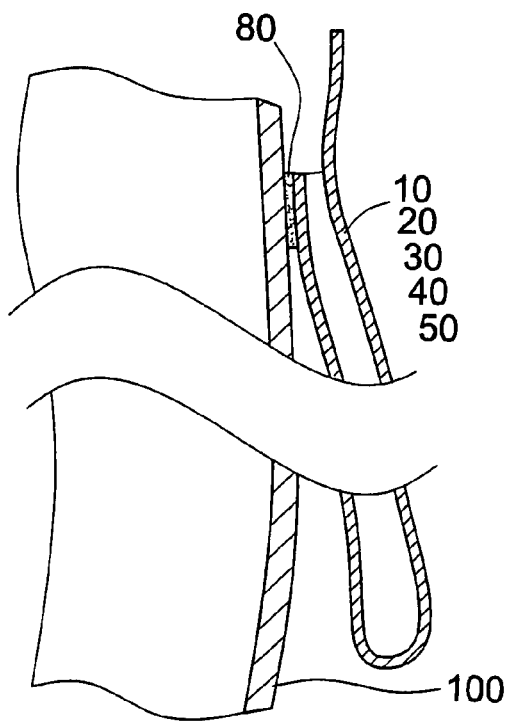
FIG. 9 is a cross-sectional view of a second attachment method for attaching any of the embodiments illustrated in FIGS. 1 through 5 which illustrates an adhesive attachment of the stethoscope cover to the isolation garments.
Figure 10:
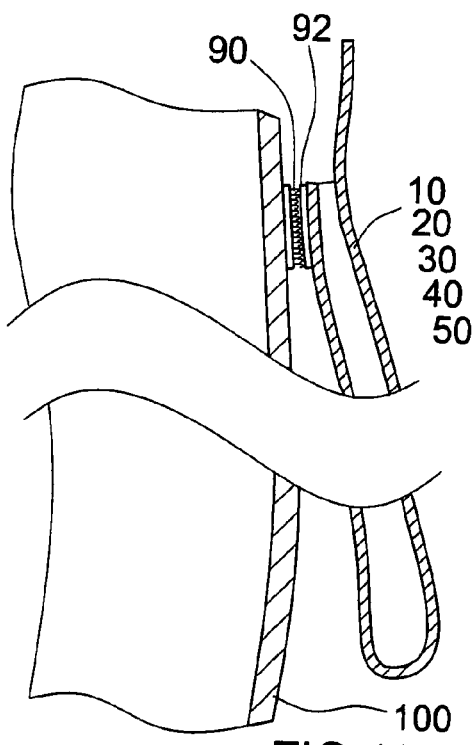
FIG. 10 is a cross-sectional view of a third attachment method for attaching any of the embodiments illustrated in FIGS. 1 through 5 which illustrates mating hook and loop fasteners by which the stethoscope cover is attached to the isolation garment.

The sheath 12 can be incorporated into and made a pat of the torso portion 130 of the isolation garment 100 or attached by any methods, three of which are illustrated in FIGS. 8 through 10 and will be discussed below. The majority of the length of the sheath 12 moves free of the torso section. As illustrated in FIG. 1, the interior listening device 152 and center sound tube 154 of the stethoscope are placed through the top opening in and are retained in the elongated interior chamber 14 and the optional exterior covering slip covers all of the upper portion of the center sound tube 140 until it attaches to the first lateral sound tubes 156 and second lateral sound tube 160. The only exposed portions are the lateral sound tube 156 and 160 and these do not come in contact with the patient. The doctor or nurse presses the lower exterior portion of the elongated sheath 12 housing the listening device 152 against the body location of the patient to listen to the patient's heart or other organs or body parts so that all portions of the stethoscope which touch or are near the patient are covered by the cover or sheath 10. Once the examination is concluded, the stethoscope 150 is removed from the cover or pouch 10 and the entire isolation garment 100 including the incorporated cover 10 are discarded and the stethoscope 150 can be reused.

Variations on the above invention are illustrated in FIGS. 2 through 6. Referring to FIG. 2, there is illustrated a second embodiment 20 of the stethoscope cover, which has an elongated sheath section 22, an elongated interior chamber 24 which is open at the top and an optional exterior covering flap 26. The stethoscope 150 is retained in the same manner as illustrated in FIG. 1. The difference in the second embodiment 20 is that it is incorporated into or attached to the isolation garment 100 at the location of the neck opening 140 so as to cover the maximum amount of the center sound tube 154.

Referring to FIG. 3, there is illustrated a third embodiment 30 of the stethoscope cover, which has an elongated sheath 32, an elongated interior chamber 34 which is open at the top and an optional exterior covering flap 36. The stethoscope 150 is retained in the same manner as illustrated in FIG. 1. The difference in the third embodiment 30 is that it is incorporated into or attached to the isolation garment 100 at an off center location of the torso portion 130. In this case, it is located on one side of the torso portion 130. It will be appreciated that the embodiment in FIG. 3 is intended to illustrate attachment of the cover 30 at any location of the torso portion 130.

Referring to FIG. 4, there is illustrated a fourth embodiment 40 of the stethoscope cover, which has an elongated sheath section 42, an elongated interior chamber 44 which is open at the top and an optional exterior covering flap 46. The stethoscope 150 is retained in the same manner as illustrated in FIG. 1. The difference in the fourth embodiment 40 is that it is incorporated into or attached to a location on a sleeve of the isolation garment 100. While it is shown on sleeve 110, it will be appreciated that the cover 40 can also be on sleeve 120.

Referring to FIG. 5, there is illustrated a fifth embodiment 50 of the stethoscope cover, which has an elongated sheath section 52, an elongated interior chamber 54 which is open at the top and an optional covering flap 56. In the previous embodiments, the sheath was in an unfolded condition both prior to use and during use. In the embodiment illustrated in FIG. 5, the sheath 52 is folded up in an accordion fashion and retained closed by first closing means 58 and second mating closing means 59 located at opposite lengthwise portions of the sheath so that the sheath 50 does not hang down from the isolation garment 100 when not in use. By way of example, the closing means 58 can be mating hook and loop fasteners. When it is desired to use cover 50, the fastener means 58 and 59 are opened so the cover then hangs down from the isolation garment 100 and the stethoscope 150 is inserted into interior chamber 52 in the manner illustrated in FIG. 1. It will also be appreciated that the fold up embodiment of the cover 50 can be at any location on the isolation garment such as the torso section near the breast plate as illustrated in FIG. 5, near the neck opening 140 as illustrated in FIG. 2, at another location on the torso section 130 as illustrated in FIG. 3, or on a sleeve 110 or 120 as illustrated in FIG. 4.

Referring to FIGS. 6 and 7, there is illustrated a sixth embodiment 60 of the stethoscope cover, which has an elongated sheath section 62 and an opening 66 leading to an elongated interior chamber 66. In this variation, the sheath or cover 60 is within the isolation garment 100 instead of being outside the isolation garment as with the embodiments illustrated in FIGS. 1 through 5. As illustrated in FIG. 6, the stethoscope 150 is retained in the cover 60 in a manner similar to the illustration in FIG. 1. This is a more difficult to use embodiment since it requires a portion of the isolation garment 100 adjacent to a portion of the sheath 62 to come in contact with the patient. In addition, while illustrated with an opening 66 in the center breast plate area of the torso, it will be appreciated that the opening 66 can be at any location of the torso 130 or sleeves 110 or 120 of the isolation garment 100. In this embodiment, the sheath 60 is formed into and is a part of the isolation garment in the same manner as the sleeves are formed into and are a part of the isolation garment.

FIGS. 8 through 10 illustrate various alternative embodiments by which any of the sheaths or covers 10, 20, 30, 40 or 50 can be incorporated into or attached as part of the isolation garment 100. In the embodiment illustrated in FIG. 8, the cover 10, 20, 30, 40 or 50 is heat shrunk and attached to the isolation garment 100 at any location on the torso 130 or sleeve 110 or 120 by heat attachment. Also at attachment site 70, the cover can be formed into and incorporated as part of the isolation garment 100, the same manner as the sleeves are incorporated into the isolation garment.

In the embodiment illustrated in FIG. 9, the cover 10, 20, 30, 40 or 50 is attached to the isolation garment 100 at any location on the torso 130 or sleeve 100 or 120 by adhesive means 80 which can be glue, spay on adhesive, double sided tape, etc.

In the embodiment illustrated in FIG. 10, the cover 10, 20, 30, 40 or 50 is attached by mating hook and loop fasteners, with one fastener 90 attached to a portion of the isolation garment 100 such as the torso section 130, sleeve 110 or sleeve 120 and the mating fastener 92 attached to the rear portion of the cover. In this embodiment, the cover is removable. It will be appreciated that other mating fasteners such as snap fasteners are also within the spirit and scope of the present invention.

Figure 11:
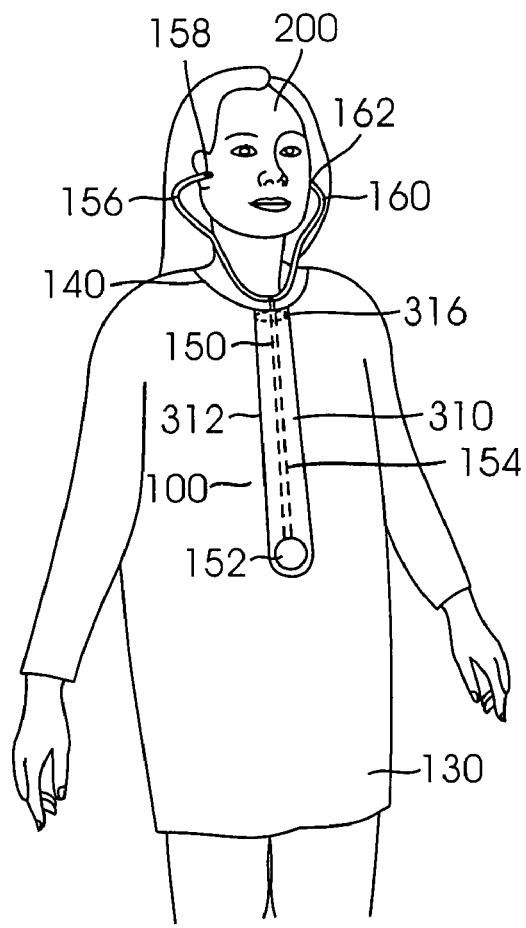
FIG. 11 is a perspective view of a seventh embodiment of the present invention stethoscope cover incorporated into an isolation garment with the portion of the stethoscope which is enclosed in the cover shown in dashed lines, the cover being attached to the center area of the torso and having its opening at the neck opening of the isolation garment.
Figure 12:
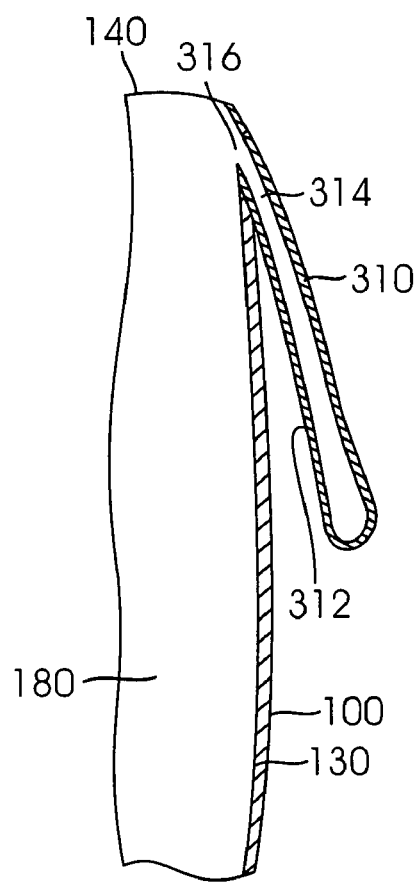
FIG. 12 is a cross-section view of the seventh embodiment of the present invention stethoscope cover illustrated in FIG. 11.

Referring to FIGS. 11 and 12, there is illustrated a seventh embodiment of the stethoscope cover or sheath 310. The sheath 310 has an elongated section 312 having an elongated interior chamber 314 which has an opening 316 at the top. In the seventh embodiment, the sheath 312 is attached so that its opening 316 is at the neck opening 140 of the isolation garment 100. In this way, when the stethoscope 150 is inserted into the sheath 310, the lateral sound tubes 156 and 160 are adjacent the opening 316 and the listening device 152 is at the bottom of the elongated interior chamber 314 and the sheath 310 is at a very functional position since the stethoscope 150 is immediately inserted into the sheath from inside the torso section 130. The sheath 310 is incorporated into the isolation garment so that the sheath 310 is articulatable to enable the stethoscope 150 to be carried in the sheath and also permits the stethoscope 150 to be used for examination purposes so that when the stethoscope 150 is inserted into the elongated interior chamber 314 so that the listening device 152 and at least a portion of the center sound tube 154 are retained in the elongated chamber 314 and at least a portion of the lateral sound tubes 156 and 160 extend out of the cover so that the listening device 152 and the sound tube 154 of the stethoscope are retained in an in-use condition to permit the stethoscope to be used for examination purposes while the stethoscope is retained in the sheath. The isolation garment 100 and the incorporated stethoscope cover 310 are disposable. Through this embodiment, the center sound tube 154 is never outside the isolation garment 100 and the sheath 310 since the center sound tube 154 is inserted from within the isolation garment 100 since the opening 316 of the sheath 310 leads directly into the isolation garment 100.

In alternative variations, the sheath 310 can be attached to the torso section 130 of the isolation garment 100 by heat shrinking means or by adhesive means.

Figure 13:
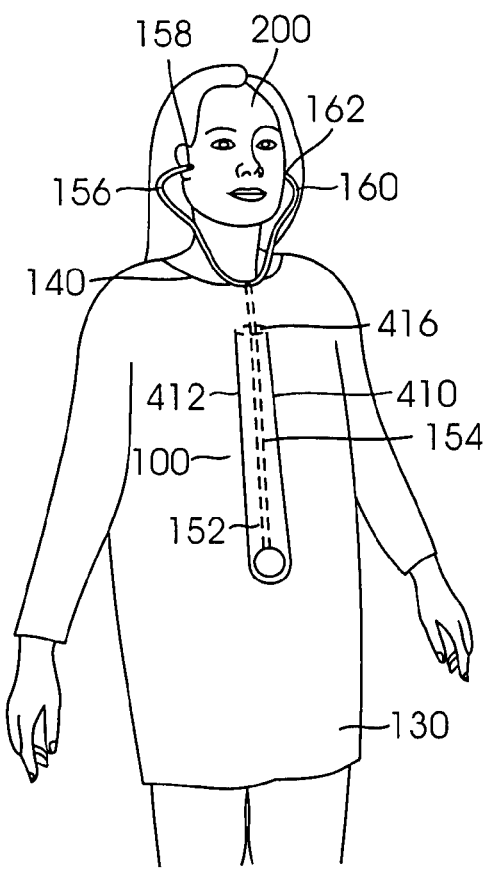
FIG. 13 is a perspective view of an eighth embodiment of the present invention stethoscope cover incorporated into an isolation garment with the portion of the stethoscope which is enclosed in the cover shown in dashed lines, the cover being attached to the center area of the torso and having its opening at a location below the neck opening of the isolation garment.
Figure 14:
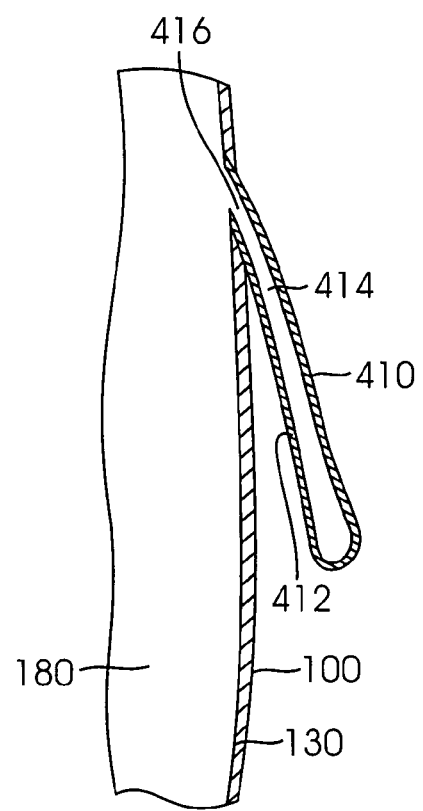
FIG. 14 is a cross-section view of the eighth embodiment of the present invention stethoscope cover illustrated in FIG. 13.

Referring to FIGS. 13 and 14, there is illustrated an eighth embodiment of the stethoscope cover or sheath 410. The sheath 410 has an elongated section 412 having an elongated interior chamber 414 which has an opening 416 at the top. In the eighth embodiment, the sheath 412 is attached so that its opening 416 is within the front torso section 130 of the isolation garment 100 at a location slightly below the neck opening 140 of the isolation garment 100 so that the opening 416 leads into the interior 180 of the isolation garment 100. In this way, when the stethoscope 150 is inserted into the sheath 410, the lateral sound tubes 156 and 160 are adjacent the opening 416 and the listening device 152 is at the bottom of the elongated interior chamber 414 and the sheath 410 is at a very functional position since the stethoscope 150 is immediately inserted into the sheath from inside the torso section 130. The sheath 410 is incorporated into the isolation garment so that the sheath 410 is articulatable to enable the stethoscope 150 to be carried in the sheath and also permits the stethoscope 150 to be used for examination purposes so that when the stethoscope 150 is inserted into the elongated interior chamber 414 so that the listening device 152 and at least a portion of the center sound tube 154 are retained in the elongated chamber 414 and at least a portion of the lateral sound tubes 156 and 160 extend out of the cover so that the listening device 152 and the sound tube 154 of the stethoscope are retained in an in-use condition to permit the stethoscope to be used for examination purposes while the stethoscope is retained in the sheath. The isolation garment 100 and the incorporated stethoscope cover 410 are disposable. Through this embodiment, the center sound tube 154 is never outside the isolation garment 100 and the sheath 410 since the center sound tube 154 is inserted from within the isolation garment 100 since the opening 416 of the sheath 410 leads directly into the isolation garment 100.

In alternative variations, the sheath 410 can be attached to the torso section 130 of the isolation garment 100 by heat shrinking means or by adhesive means.

Defined in detail, the present invention is a stethoscope cover for use with an isolation garment having a torso section with a neck opening, and for use with a stethoscope having a listening device attached to a center sound tube attached to a first and second lateral sound tube, each lateral sound tube terminating in an ear piece, the stethoscope cover comprising: (a) an elongated sheath section with an opening leading to an elongated interior chamber; (b) means by which the elongated sheath is incorporated into or attached to the torso section of the isolation garment so that the opening of the sheath is at the neck opening of the isolation garment; (c) the isolation garment and incorporated stethoscope cover are disposable; and (d) the sheath incorporated into the isolation garment so that the sheath is articulatable to enable the stethoscope to be carried in the sheath and also permit the stethoscope to be used for examination purposes so that when the stethoscope is inserted into the elongated interior chamber so that the listening device and at least a portion of the center sound tube are retained in the elongated interior chamber and at least a portion of the lateral sound tubes extend out of the cover, the listening device and the sound tube of the stethoscope are retained in an in-use condition to permit the stethoscope to be used for examination purposes while the stethoscope is retained in the sheath.

Also alternatively defined in detail, the present invention is a stethoscope cover for use with an isolation garment having a torso section with a neck opening and an interior, and for use with a stethoscope having a listening device attached to a center sound tube attached to a first and second lateral sound tube, each lateral sound tube terminating in an ear piece, the stethoscope cover comprising: (a) an elongated sheath section with an opening leading to an elongated interior chamber; (b) means by which the elongated sheath is incorporated into or attached to the torso section of the isolation garment so that the opening of the sheath is below the neck opening of the isolation garment and extends into the interior of the isolation garment; (c) the isolation garment and incorporated stethoscope cover are disposable; and (d) the sheath incorporated into the isolation garment so that the sheath is articulatable to enable the stethoscope to be carried in the sheath and also permit the stethoscope to be used for examination purposes so that when the stethoscope is inserted into the elongated interior chamber so that the listening device and at least a portion of the center sound tube are retained in the elongated interior chamber and at least a portion of the lateral sound tubes extend out of the cover, the listening device and the sound tube of the stethoscope are retained in an in-use condition to permit the stethoscope to be used for examination purposes while the stethoscope is retained in the sheath.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

What is claimed is:

1. A stethoscope cover for use with an isolation garment having a torso section with a neck opening, and for use with a stethoscope having a listening device attached to a center sound tube attached to a first and second lateral sound tube, each lateral sound tube terminating in an ear piece, the stethoscope cover comprising:
   a. an elongated sheath section having an elongated body with an opening leading to an elongated interior chamber;
   b. means by which the elongated sheath is incorporated into or attached to the torso section of the isolation garment so that the opening of the sheath is at the neck opening of the isolation garment and the elongated body extending outside of, in front of and not attached to the torso section of the isolation garment;
   c. the isolation garment and incorporated stethoscope cover are disposable; and
   d. the sheath incorporated into the isolation garment so that the sheath is articulatable to enable the stethoscope to be carried in the sheath and also permit the stethoscope to be used for examination purposes so that when the stethoscope is inserted into the elongated interior chamber so that the listening device and at least a portion of the center sound tube are retained in the elongated interior chamber and at least a portion of the lateral sound tubes extend out of the cover, the listening device and the sound tube of the stethoscope are retained in an in-use condition to permit the stethoscope to be used for examination purposes while the stethoscope is retained in the sheath.

2. The stethoscope cover in accordance with claim 1, wherein said elongated sheath is attached to the isolation garment by heat shrinking means.

3. The stethoscope cover in accordance with claim 1, wherein said elongated sheath is attached to the isolation garment by adhesive means.

4. A stethoscope cover for use with an isolation garment having a torso section with a neck opening and an interior, and for use with a stethoscope having a listening device attached to a center sound tube attached to a first and second lateral sound tube, each lateral sound tube terminating in an ear piece, the stethoscope cover comprising:
   a. an elongated sheath section having an elongated body with an opening leading to an elongated interior chamber;
   b. means by which the elongated sheath is incorporated into or attached to the torso section of the isolation garment so that the opening of the sheath is below the neck opening of the isolation garment and extends into the interior of the isolation garment and the elongated body extending outside of, in front of and not attached to the torso section of the isolation garment;
   c. the isolation garment and incorporated stethoscope cover are disposable; and
   d. the sheath incorporated into the isolation garment so that the sheath is articulatable to enable the stethoscope to be carried in the sheath and also permit the stethoscope to be used for examination purposes so that when the stethoscope is inserted into the elongated interior chamber so that the listening device and at least a portion of the center sound tube are retained in the elongated interior chamber and at least a portion of the lateral sound tubes extend out of the cover, the listening device and the sound tube of the stethoscope are retained in an in-use condition to permit the stethoscope to be used for examination purposes while the stethoscope is retained in the sheath.

5. The stethoscope cover in accordance with claim 4, wherein said elongated sheath is attached to the isolation garment by heat shrinking means.

6. The stethoscope cover in accordance with claim 4, wherein said elongated sheath is attached to the isolation garment by adhesive means.

* * * * *